United States Patent
Onda (10) Patent No.: US 10,252,965 B2
(45) Date of Patent: Apr. 9, 2019

(54) VINYLBENZYLATED PHENOL COMPOUND, METHOD OF MANUFACTURING VINYLBENZYLATED PHENOL COMPOUND, ACTIVATED ESTER RESIN, METHOD OF MANUFACTURING ACTIVATED ESTER RESIN, THERMOSET RESIN COMPOSITION, HARDENED MATERIAL OF THERMOSET RESIN COMPOSITION, INTERLAYER INSULATING MATERIAL, PREPREG, AND METHOD OF MANUFACTURING PREPREG

(71) Applicant: AIR WATER INC., Sapporo-shi, Hokkaido (JP)

(72) Inventor: Shinji Onda, Kashima (JP)

(73) Assignee: AIR WATER INC., Sapporo-shi, Hokkaido (JP)

(*) Notice: Subject to any disclaimer, the term of this patent is extended or adjusted under 35 U.S.C. 154(b) by 155 days.

(21) Appl. No.: 15/346,422

(22) Filed: Nov. 8, 2016

(65) Prior Publication Data

US 2017/0129837 A1 May 11, 2017

(30) Foreign Application Priority Data

Nov. 11, 2015 (JP) ................................. 2015-220859
Nov. 4, 2016 (JP) ................................. 2016-216213

(51) Int. Cl.

| | | |
|---|---|---|
| B32B 27/38 | (2006.01) |
| B32B 27/36 | (2006.01) |
| B32B 27/26 | (2006.01) |
| C08J 5/24 | (2006.01) |
| C08L 63/00 | (2006.01) |
| C08L 67/03 | (2006.01) |
| C08L 67/06 | (2006.01) |
| C08L 67/07 | (2006.01) |
| C07C 37/11 | (2006.01) |
| C07C 39/00 | (2006.01) |
| C07C 39/205 | (2006.01) |
| C07C 39/225 | (2006.01) |
| C07C 39/21 | (2006.01) |
| C08G 63/547 | (2006.01) |
| C07C 67/14 | (2006.01) |
| C07C 37/18 | (2006.01) |
| C08G 59/42 | (2006.01) |

(52) U.S. Cl.
CPC .............. *C07C 39/21* (2013.01); *C07C 37/18* (2013.01); *C07C 39/225* (2013.01); *C07C 67/14* (2013.01); *C08G 59/4223* (2013.01); *C08G 59/4276* (2013.01); *C08G 63/547* (2013.01); *C08J 5/24* (2013.01); *C08L 63/00* (2013.01); *C08L 67/06* (2013.01); *C08J 2363/00* (2013.01); *C08J 2467/03* (2013.01); *C08J 2467/07* (2013.01)

(58) Field of Classification Search
None
See application file for complete search history.

(56) References Cited

U.S. PATENT DOCUMENTS 4,054,676 A * 10/1977 Weinshenker ........ A23L 3/3463
252/404

FOREIGN PATENT DOCUMENTS

| JP | 2001-281860 A | 10/2001 |
| JP | 5120520 B | 1/2013 |
| JP | 2014-062243 A | 4/2014 |

OTHER PUBLICATIONS

Kun: "Macroreticular Redox Polymers. I. Hydroquinone-Quinone Redox Polymers"; Journal of Polymer Science: Part A vol. 3, pp. 1833-1845. (Year: 1965).*
Jong-Man Kim et al., "Transient Protection of Intramolecular Hydrogen Bonding: A Simple but Elegant Approach for Functional Imaging", Macromolecular Research, vol. 12, No. 5, pp. 493-500, Oct. 2004.
Translation of 1st Office Action issued in corresponding Taiwan Application No. 105136449, Jul. 14, 2017 (4 pages).

* cited by examiner

*Primary Examiner* — Michael J Feely
(74) *Attorney, Agent, or Firm* — Hamre, Schumann, Mueller & Larson, P.C.

(57) ABSTRACT

A vinylbenzylated phenol compound represented by General Formula (1) below is provided.

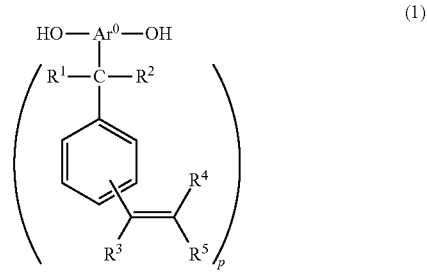

(In General Formula (1), $Ar^0$ is a bifunctional phenol compound residue having one or more monocyclic or polycyclic aromatic nuclei, $R^1$ to $R^5$ may be the same or different and are each hydrogen or a methyl group, and p is an integer of 1 to 4.)

13 Claims, 4 Drawing Sheets

VINYLBENZYLATED PHENOL COMPOUND, METHOD OF MANUFACTURING VINYLBENZYLATED PHENOL COMPOUND, ACTIVATED ESTER RESIN, METHOD OF MANUFACTURING ACTIVATED ESTER RESIN, THERMOSET RESIN COMPOSITION, HARDENED MATERIAL OF THERMOSET RESIN COMPOSITION, INTERLAYER INSULATING MATERIAL, PREPREG, AND METHOD OF MANUFACTURING PREPREG

TECHNICAL FIELD

The present invention relates to an active ester resin that is useful as a component of a thermoset resin composition, a method of manufacturing the active ester resin, a vinylbenzylated phenol compound that is one of raw materials for manufacturing the active ester resin, a method of manufacturing the vinylbenzylated phenol compound, a thermoset resin composition that contains the above active ester resin, a hardened material of the thermoset resin composition, an interlayer insulating material that is formed using the thermoset resin composition, a prepreg that is formed using the thermoset resin composition, and a method of manufacturing the prepreg.

BACKGROUND ART

In accordance with the performance improvement, such as enhanced functionality and density, of information communication devices in recent years, printed wiring boards are also required to have performance responsible thereto. A hardened material of a thermoset resin composition is used as an insulating material that forms a printed wiring board. Among thermoset resin compositions, an epoxy-based resin composition that contains an epoxy-based compound is widely used in view of the cost and adhesiveness. In particular, multilayer wiring boards are recently developed to correspond to the reduced thickness and size and enhanced performance of electronic devices.

JP5120520B describes using, for example, an active ester resin as the hardening agent for such an epoxy-based resin composition. It is said that, by using the ester resin as disclosed in this patent literature, a thermoset resin composition having both excellent heat resistance and flame retardance can be obtained while the hardened material has low permittivity and low dielectric tangent.

JP5120520B describes that the above ester resin is generated by reacting a phenolic hydroxyl group-containing substance and aromatic dicarboxylic acid or aromatic dicarboxylic acid chloride.

JP2014-62243A, on the other hand, describes an aromatic vinylbenzyl ether compound that gives a hardened material having excellent dielectric characteristics (low permittivity/low dielectric tangent) even after moisture absorption under a high-temperature and high-humidity environment and also having a high glass-transition temperature and flame retardance.

SUMMARY OF INVENTION

The present invention provides an active ester resin useful as a component of a thermoset resin composition that can form a hardened material having excellent dielectric characteristics and excellent heat resistance, a method of manufacturing the active ester resin, a vinylbenzylated phenol compound that is one of raw materials for manufacturing the active ester resin, a method of manufacturing the vinylbenzylated phenol compound, a thermoset resin composition that contains the above active ester resin, a hardened material of the thermoset resin composition, an interlayer insulating material that is formed using the thermoset resin composition, a prepreg that is formed using the thermoset resin composition, and a method of manufacturing the prepreg.

The present invention provided here is as follows.

In one aspect, the present invention provides [1] a vinylbenzylated phenol compound represented by General Formula (1) below, where, in General Formula (1), $Ar^0$ is a bifunctional phenol compound residue having one or more monocyclic or polycyclic aromatic nuclei, $R^1$ to $R^5$ may be the same or different and are each hydrogen or a methyl group, and p is an integer of 1 to 4.

In one aspect, the present invention provides [2] the vinylbenzylated phenol compound as recited in the above [1], wherein $Ar^0$ in General Formula (1) is a structure represented by General Formula (2), General Formula (3) or General Formula (11) below, where Y in General Formula (3) is a direct bond, —$CH_2$—, —$C(CH_3)_2$—, —$CH(CH_3)$—, an ether bond, a fluorenyl group, a sulfone group, a cyclohexylidene group, a 3,3,5-trimethylcyclohexylidene group, —$C(CF_3)_2$—, or —$C(CH_3)(Ph)$-; or a structure represented by General Formula (21), General Formula (22) or General Formula (23) below.

(22)

(23)

($R^{26}$ to $R^{33}$ may be the same or different and are each hydrogen or a methyl group.)

(11)

(Where Z in General Formula (11) is a direct bond, —$CH_2$—, —$C(CH_3)_2$—, —$CH(CH_3)$— —$CH(Ph)$-, —$C(CH_3)(Ph)$-, a fluorenyl group, a cyclohexylidene group, or 3,3,5-trimethylcyclohexylidene group; or a structure represented by General Formula (21), General Formula (22) or General Formula (23) above.)

In one aspect, the present invention provides [3] a method of manufacturing the vinylbenzylated phenol compound of the above [1] or [2], the method comprising reacting a bifunctional phenol compound having one or more monocyclic or polycyclic aromatic nuclei and a vinylbenzyl halide compound using any hydrotalcite as a dehydrohalogenation agent.

In one aspect, the present invention provides [4] the method of manufacturing the vinylbenzylated phenol compound as recited in the above [3], wherein the bifunctional phenol compound having one or more monocyclic or polycyclic aromatic nuclei is represented by General Formula (4), General Formula (5) or General Formula (12) below,

(4)

(5)

where Y in General Formula (5) is a direct bond, —$CH_2$—, —$C(CH_3)_2$—, —$CH(CH_3)$—, an ether bond, a fluorenyl group, a sulfone group, a cyclohexylidene group, a 3,3,5-trimethylcyclohexylidene group, —$C(CF_3)_2$—, or —$C(CH_3)(Ph)$-; or a structure represented by General Formula (21), General Formula (22) or General Formula (23) below.

(21)

(22)

(23)

($R^{26}$ to $R^{33}$ may be the same or different and are each hydrogen or a methyl group.)

(12)

(Where Z in General Formula (12) is a direct bond, —$CH_2$—, —$C(CH_3)_2$—, —$CH(CH_3)$— —$CH(Ph)$-, —$C(CH_3)(Ph)$-, a fluorenyl group, a cyclohexylidene group, or 3,3,5-trimethylcyclohexylidene group; or a structure represented by General Formula (21), General Formula (22) or General Formula (23) above.)

In one aspect, the present invention provides [5] an active ester resin comprising a component represented by General Formula (6) below, (6)

where, in General Formula (6), X is a structure represented by General Formula (7), General Formula (8) or General Formula (13) below, $Ar^1$ and $Ar^2$ may be the same or different and are each a phenyl group, a phenyl group having one to three alkyl groups each with one to four carbon atoms on an aromatic nucleus, a naphthyl group, or a naphthyl group having one to three alkyl groups each with one to four carbon atoms on an aromatic nucleus, and an average number of repetition n is 0.5 to 30, (7)

(8)

where, in General Formula (7) and General Formula (8), $R^1$ to $R^{15}$ may be the same or different and are each hydrogen or a methyl group, an average number of repetition m is 0.1 to 4, and an average number of repetition l and an average number of repetition k are each independently 0.1 to 2, and Y in General Formula (8) is a direct bond, —$CH_2$—, —$C(CH_3)_2$—, —$CH(CH_3)$—, an ether bond, a fluorenyl group, a sulfone group, a cyclohexylidene group, a 3,3,5-trimethylcyclohexylidene group, —$C(CF_3)_2$—, or —$C(CH_3)(Ph)$-; or a structure represented by General Formula (21), General Formula (22) or General Formula (23) below.

(21)

(22)

(23)

($R^{26}$ to $R^{33}$ may be the same or different and are each hydrogen or a methyl group.)

(13)

(Where Z in General Formula (13) is a direct bond, —$CH_2$—, —$C(CH_3)_2$—, —$CH(CH_3)$— —$CH(Ph)$-, —$C(CH_3)(Ph)$-, a fluorenyl group, a cyclohexylidene group, or a 3,3,5-trimethylcyclohexylidene group; or a structure represented by General Formula (21), General Formula (22) or General Formula (23) above, and $R^{16}$ to $R^{25}$ may be the same or different and are each hydrogen or a methyl group, and average numbers of repetition j and I are each independently 0.1 to 2.)

In another aspect, the present invention provides [6] the active ester resin as described in the above [5], wherein X in General Formula (6) has a structure represented by General Formula (7).

In another aspect, the present invention provides [7] a method of manufacturing an active ester resin, characterized by reacting the vinylbenzylated phenol compound as described in the above [1] or the above [2], a monofunctional phenol compound, and one or more selected from the group consisting of an aromatic nucleus-containing dicarboxylic acid and a halide compound thereof.

In another aspect, the present invention provides [8] a thermoset resin composition characterized by including the active ester resin as described in the above [5] or the above [6] and an epoxy resin.

In another aspect, the present invention provides [9] the thermoset resin composition as described in the above [8], further including a hardening accelerator.

In another aspect, the present invention provides [10] the thermoset resin composition as described in the above [8] or the above [9], further including an inorganic filler.

In another aspect, the present invention provides [11] a hardened material of the thermoset resin composition as described in any one of the above [8] to the above [10].

In another aspect, the present invention provides [12] an interlayer insulating material characterized by containing the thermoset resin composition as described in any one of the above [8] to the above [10].

In another aspect, the present invention provides [13] a prepreg characterized by comprising: a semi-hardened body of the thermoset resin composition as described in any one of the above [8] to the above [10]; and a fibrous reinforcing member.

In another aspect, the present invention provides [14] a method of manufacturing a prepreg, characterized by impregnating a fibrous reinforcing material with the thermoset resin composition as described in any one of the above [8] to the above [10] and heating them to semi-harden the thermoset resin composition impregnated in the fibrous reinforcing material.

In another aspect, the present invention provides [15] a composition comprising plural kinds of compounds having a different number of substitutions of the structural moiety, described in the bracket of General Formula (1) of the above [1], on the aromatic nuclei, wherein an average repetition number of the structural portion is 0.1 to 4.

According to the present invention, there is provided an active ester resin useful as a component of a thermoset resin composition that can form a hardened material having excellent dielectric characteristics (permittivity and dielectric tangent) and excellent heat resistance (glass-transition temperature and weight reduction under high-temperature environments), a method of manufacturing the active ester resin, a vinylbenzylated phenol compound that is one of raw materials for manufacturing the active ester resin, a method of manufacturing the vinylbenzylated phenol compound, a thermoset resin composition that contains the above active ester resin, a hardened material of the thermoset resin composition, an interlayer insulating material that is formed using the thermoset resin composition, a prepreg that is formed using the thermoset resin composition, and a method of manufacturing the prepreg.

DETAILED DESCRIPTION OF INVENTION

Embodiments of the present invention will be described hereinafter.

Vinylbenzylated phenol compound (a) according to one embodiment of the present invention is represented by General Formula (1) below.

(1)

In General Formula (1), $Ar^0$ is a bifunctional phenol compound residue having one or more monocyclic or polycyclic aromatic nuclei. $R^1$ to $R^5$ may be the same or different and are each hydrogen or a methyl group. p is an integer of 1 to 4. A composition of one aspect of the present invention comprises plural kinds of compounds having a different number of substitutions of the structural moiety, described in the bracket of General Formula (1), on the aromatic nuclei, wherein an average repetition number of the structural portion is 0.1 to 4. The reason that the average number of repetition can be non-integer is because the vinylbenzylated phenol compound (a) may be composed of a composition that includes a plurality types of compounds of which the number of bonds to the aromatic nuclei in the parenthetic structural site of General Formula (1) is different. The same applies to the average numbers of repetition in other general formulae.

Specific examples of $Ar^0$ include structures represented by General Formula (2), General Formula (3) or General Formula (11) below.

(2)

(3)

Locations of two hydroxyl groups on the aromatic nuclei in General Formula (2) and General Formula (3) are freely selected. Y in General Formula (3) is a direct bond (in this case, the structure represented by General Formula (3) is a biphenylylene group), —CH$_2$—, —C(CH$_3$)$_2$—, —CH(CH$_3$)—, an ether bond, a fluorenyl group, a sulfone group, a cyclohexylidene group, a 3,3,5-trimethylcyclohexylidene group, —C(CF$_3$)$_2$— or —C(CH$_3$)(Ph)-; or a structure represented by General Formula (21), General Formula (22) or General Formula (23) below.

(21)

(22)

(23)

In General Formula (21), General Formula (22) and General Formula (23) above, $R^{26}$ to $R^{33}$ may be the same or different and are each hydrogen or a methyl group.

(11)

In General Formula (11), Z is a direct bond, —CH$_2$—, —C(CH$_3$)$_2$—, —CH(CH$_3$)——CH(Ph)-, —C(CH$_3$)(Ph)-, a fluorenyl group, a cyclohexylidene group, or 3,3,5-trimethylcyclohexylidene group; or a structure represented by General Formula (21), General Formula (22) or General Formula (23) above.

Method of manufacturing the above vinylbenzylated phenol compound (a) according to one embodiment of the present invention is not limited. The vinylbenzylated phenol compound (a) can be efficiently manufactured by the manufacturing method which will be described below.

The method of manufacturing the vinylbenzylated phenol compound (a) according to one embodiment of the present invention includes reacting a bifunctional phenol compound (α) having one or more monocyclic or polycyclic aromatic nuclei and a vinylbenzyl halide compound (β) using any hydrotalcite (γ) as a dehydrohalogenation agent.

Specific type of the above bifunctional phenol compound (α) is not limited. Specific examples thereof include compounds represented by General Formula (4), General Formula (5), General Formula (12) below.

(4)

(5)

Here, Y in General Formula (5) includes a direct bond (in this case, the compound represented by General Formula (5) includes biphenol), —$CH_2$— (in this case, the compound represented by General Formula (5) includes bisphenol F), —$C(CH_3)_2$— (in this case, the compound represented by General Formula (5) includes bisphenol A), —$CH(CH_3)$— (in this case, the compound represented by General Formula (5) includes bisphenol E), an ether bond, a fluorenyl group, a sulfone group (in this case, the compound represented by General Formula (5) includes bisphenol S), a cyclohexylidene group (in this case, the compound represented by General Formula (5) includes bisphenol Z), a 3,3,5-trimethylcyclohexylidene group (in this case, the compound represented by General Formula (5) includes bisphenol TMC), —$C(CF_3)_2$— (in this case, the compound represented by General Formula (5) includes bisphenol AF), —$C(CH_3)(Ph)$- (in this case, the compound represented by General Formula (5) includes bisphenol AP). In General Formula (5) above, Y includes a structure represented by General Formula (21), General Formula (22), or General Formula (23) below such as a 1,3-phenylenediisopropylidene group (in this case, the compound represented by General Formula (5) includes bisphenol M), or a 1,4-phenylenediisopropylidene group (in this case, the compound represented by General Formula (5) includes bisphenol P).

(21)

(22)

(23)

In General Formula (21), General Formula (22) and General Formula (23) above, $R^{26}$ to $R^{33}$ may be the same or different and are each hydrogen or a methyl group.

(12)

In General Formula (12), Z is a direct bond, —$CH_2$—, —$C(CH_3)_2$—, —$CH(CH_3)$— —$CH(Ph)$-, —$C(CH_3)(Ph)$-, a fluorenyl group, a cyclohexylidene group, or 3,3,5-trimethylcyclohexylidene group; or a structure represented by General Formula (21), General Formula (22) or General Formula (23) above.

The vinylbenzyl halide compound (β) may be configured such that a vinyl group and a halogenated methyl group are bonded to an aromatic nucleus, and the positional relationship between the vinyl group and the halogenated methyl group is not limited.

In the manufacturing method according to one embodiment of the present invention, any hydrotalcite (γ) is used as a dehydrohalogenation agent for the reaction of the above bifunctional phenol compound (α) and vinylbenzyl halide compound (β). The hydrotalcite (γ) is a hydrate of a complex of magnesium and aluminum carbonate and hydroxide, and its general formula is $Mg_5Al_{12}(OH)_{16}(CO_3).4H_2O$ or $Mg_{4.5}Al_2(OH)_{13}CO_3.qH_2O$ (q is 3 to 3.5). Examples of nonhydrate thereof include $Mg_{0.7}Al_{0.3}O_{1.15}$. Examples of specific products of the hydrotalcite (γ) include KW-500SH, KW-500SN, KW-500PL, KW-500G-7, KW-1000, KW-1015, KW-2000, and KW-2100 (all available from Kyowa Chemical Industry Co., Ltd). Using the hydrotalcite (γ) as a dehydrohalogenation agent allows the residue based on the vinylbenzyl halide compound (β) to be directly bonded to the skeleton of the aromatic nucleus while phenolic hydroxyl groups of the bifunctional phenol compound (α) remain.

In this regard, the aromatic vinylbenzyl ether compound as described, for example, in JP2014-62243A is formed of a polyvalent phenol compound and a vinylbenzyl halide, and by using an alkali metal hydroxide such as sodium hydroxide as a dehydrohalogenation agent, the phenolic hydroxyl groups in the polyvalent phenol compound and halogen in the vinylbenzyl halide react to form ether bonds. In such a reaction, vinyl groups are introduced in a form in which a part of the polyvalent phenol compound is consumed, and therefore the structural controllability of the active ester resin will then be low. In contrast, according to the manufacturing method of one embodiment of the present invention, the phenolic hydroxyl group possessed by the bifunctional phenol compound (α) can be a reaction point with the carboxylic acid halide during the reaction for forming the active ester resin, thereby to allow easy molecular design of the active ester resin.

The feeding amount of raw materials and reaction condition in the reaction between the bifunctional phenol compound (α) and the vinylbenzyl halide compound (β) are appropriately set in accordance with a desired structure of the reduction produce so that the dehydrohalogenation reaction by the hydrotalcite (γ) appropriately progresses. The molar ratio (β/α) of the feeding amount of the vinylbenzyl halide compound (β) to that of the bifunctional phenol compound (α) may preferably be 0.1 to 2.0. The molar ratio (γ/β) of the use amount of the hydrotalcite (γ) to the feeding amount of the vinylbenzyl halide compound (β) may preferably be 0.70 to 1.50. When the hydrotalcite (γ) is used as a dehydrohalogenation agent, the dehydrohalogenation reaction involves generation of carbon dioxide and water, and it is therefore preferred that the reaction condition such as heating temperature is set with consideration for appropriately controlling the generation of carbon dioxide gas during the reaction, appropriately discharging the water to external of the system, and the like.

The dehydrohalogenation reaction may include, for example, but is not limited to, dropping the vinylbenzyl halide compound (β) while maintaining the temperature of a slurry-like reaction liquid that contains the bifunctional phenol compound (α) and the hydrotalcite (γ) within a range of 50° C. to 80° C., preferably within a range of 60° C. to 70° C. This operation can suppress rapid generation of carbon dioxide gas. It is also preferred to use a solvent such as toluene and methyl isobutyl ketone in the above slurry-like reaction liquid and remove water in the reaction liquid by heating the temperature of the reaction liquid to 100° C. or higher after dropping whole of the vinylbenzyl halide compound (β).

Specific examples of the bifunctional phenol compound (α) include dihydroxynaphthalenes such as 1,4-dihydroxynaphthalene, 1,5-dihydroxynaphthalene, 1,6-dihydroxynaphthalene, 1,7-dihydroxynaphthalene, 2,6-dihydroxynaphthalene and 2,7-dihydroxynaphthalene, bisphenols such as bisphenol F, bisphenol A, bisphenol E, bisphenol S, bisphenol fluorene, bisphenol Z, bisphenol TMC, bisphenol AF, bisphenol M and bisphenol P, and 4,4'-oxydiphenol. In view of the heat resistance, dielectric characteristics and availability of raw materials, 1,6-dihydroxynaphthalene, 2,7-dihydroxynaphthalene, bisphenol fluorene, and bisphenol TMC are preferred.

Examples of the solvent used for the reaction of the bifunctional phenol compound (α) and vinylbenzyl halide compound (β) include toluene, xylene, mesitylene, ethyl benzene, methyl isobutyl ketone, methyl-n-amylketone, and methylisoamylketone.

Active ester resin (A) according to one embodiment of the present invention contains a component having a structure represented by General Formula (6) below.

(6)

In General Formula (6), X is a structure represented by General Formula (7), General Formula (8), or General Formula (13) below. $Ar^1$ and $Ar^2$ may be the same or different and are each a phenyl group, a phenyl group having one to three alkyl groups each with one to four carbon atoms on an aromatic nucleus, a naphthyl group, or a naphthyl group having one to three alkyl groups each with one to four carbon atoms on an aromatic nucleus. The average number of repetition is 0.5 to 30.

(7)

(8)

In General Formula (7) and General Formula (8), $R^1$ to $R^{15}$ may be the same or different and are each hydrogen or a methyl group. The average number of repetition m is 0.1 to 4. The average number of repetition l and the average number of repetition k are each independently 0.1 to 2. As in General Formula (3) and General Formula (5), Y in General Formula (8) is a direct bond, —$CH_2$—, —$C(CH_3)_2$—, —$CH(CH_3)$—, an ether bond, a fluorenyl group, a sulfone group, a cyclohexylidene group, a 3,3,5-trimethylcyclohexylidene group, —$C(CF_3)_2$—, or —$C(CH_3)(Ph)$-; or a structure represented by General Formula (21), General Formula (22), or General Formula (23) below (21)

(22)

In General Formula (21), General Formula (22) and General Formula (23) above, $R^{26}$ to $R^{33}$ may be the same or different and are each hydrogen or a methyl group.

In General Formula (13), Z is a direct bond, —$CH_2$—, —$C(CH_3)_2$—, —$CH(CH_3)$— —$CH(Ph)$-, —$C(CH_3)(Ph)$-, a fluorenyl group, a cyclohexylidene group, or a 3,3,5-trimethylcyclohexylidene group; or a structure represented by General Formula (21), General Formula (22) or General Formula (23) above, and $R^{16}$ to $R^{25}$ may be the same or different and are each hydrogen or a methyl group, and average numbers of repetition j and l are each independently 0.1 to 2.

Unlike the active ester resin as disclosed in JP5120520B, the active ester resin (A) according to one embodiment of the present invention has a vinyl group, which is capable of polymerization reaction, at the aromatic nucleus of a benzyl group. For this reason, when the reaction progresses so that the double bond of the vinyl group is a reaction site, the relative positions of the carbon chain formed by the reaction and the main chain including the ester bond of the active ester resin (A) do not readily vary. Therefore, the hardened material of the thermoset resin composition including the active ester resin (A) according to one embodiment of the present invention is less likely to deform or decompose when heated and can thus be a material that has a high glass-transition temperature and is excellent in the heat resistance and stability. In view of enhancing stable fixation of the main chain of the active ester resin (A) (such as the difficulty in rotational movement around the main chain as the axis of rotation), the active ester resin (A) according to one embodiment of the present invention may preferably be configured such that X in General Formula (6) is a structure represented by General Formula (7).

Method of manufacturing the active ester resin (A) according to one embodiment of the present invention is not limited. For example, the active ester resin (A) can be obtained by reacting the vinylbenzylated phenol compound (a) according to one embodiment of the present invention, a monofunctional phenol compound (b), and an aromatic carboxylic acid-based compound (c) that is composed of one type selected from the group consisting of an aromatic nucleus-containing dicarboxylic acid and a halide compound thereof.

Specific examples of the monofunctional phenol compound (b) include an unsubstituted monofunctional phenol compound such as phenol and naphthol and an alkyl-substituted monofunctional phenol compound such as cresol, dimethyl phenol and ethyl phenol. It may be preferred that, in the alkyl-substituted monofunctional phenol compound, the number of substituted alkyl groups is 3 or less and the carbon number of the alkyl group is 4 or less, in view of the balance of the hardening ability and dielectric characteristics with those of an epoxy resin (B) to be described later.

Specific examples of the aromatic carboxylic acid-based compound (c) include phthalic acid, isophthalic acid, terephthalic acid, 2,6-naphthalenedicarboxylic acid, 1,6-naphthalenedicarboxylic acid, 2,7-naphthalenedicarboxylic acid, diphenylether-4,4'-dicarboxylic acid, 4,4'-biphenyldicarboxylic acid, and acid chlorides thereof.

Any condition of the above reaction is possible, provided that the active ester resin (A) can be appropriated generated. Since it is known that an active ester resin can be obtained by reacting a polyfunctional phenol compound (phenolic hydroxyl group-containing resin as in JP5120520B is exemplified), a monofunctional phenol compound (b), and an aromatic carboxylic acid-based compound (c), this manufacturing method will serve as a useful reference.

The thermoset resin composition according to one embodiment of the present invention contains the active ester resin (A) according to one embodiment of the present invention and an epoxy resin (B).

As the epoxy resin (B), any known one can be used. Examples of the epoxy resin (B) include, for example, an epoxy resin having divalent or more epoxy group, such as a bisphenol A-type epoxy resin, a bisphenol F-type epoxy resin, a phenol novolac-type epoxy resin, a cresol novolac-type epoxy resin, a biphenyl-type epoxy resin, a phenol biphenyl aralkyl-type epoxy resin, an epoxy compound of an aralkyl resin by xylilene bonding such as phenol and naphthol, an epoxy compound of a dicyclopentadiene-modified phenol resin, a dihydroxynaphthalene-type epoxy resin, a triphenol methane-type epoxy resin and other glicidyl ether-type epoxy resins, glycidyl ester-type epoxy resins, and glycidyl amine-type epoxy resins. These epoxy resins may be used alone or two or more types may be used in combination.

It is preferred to use, among these candidates of the epoxy resin (B), a resin having a large epoxy equivalent, such as a phenol biphenyl aralkyl-type epoxy resin, an epoxy compound of an aralkyl resin by xylilene bonding such as phenol and naphthol, and an epoxy compound of a dicyclopentadiene-modified phenol resin. This is because excellent dielectric characteristics are obtained when using such a resin.

With regard to the compounding ratio of the active ester resin (A) and the epoxy resin (B) in the thermoset resin composition according to one embodiment of the present invention, the equivalent ratio (B/A) between the epoxy groups included in the epoxy resin (B) and the ester groups included in the active ester resin (A) is preferably within a range of 0.5 to 1.5 and particularly preferably within a range of 0.8 to 1.2.

The thermoset resin composition according to one embodiment of the present invention may further include a hardening accelerator. From the viewpoint of promoting the reaction of vinyl groups included in the active ester resin (A), examples of the hardening accelerator include hydroperoxide, organic peroxides such as dialkyl peroxide, azo compounds, and organic boron compounds such as trialkylborane. As a hardening accelerator for the ester groups included in the active ester resin (A) and for the epoxy resin (B), known substances can be used. Examples of the hardening accelerator include a tertiary amine compound, a quaternary ammonium salt, imidazoles, a phosphine compound, and a phosphonium salt. More specific examples include tertiary amine compounds such as triethylamine, triethylenediamine, benzyldimethylamine, 4-dimetylaminopyridine, 2,4,6-tris(dimethylaminomethyl)phenol and 1,8-diazabicyclo(5,4,0)undecene-7, imidazoles such as 2-methylimidazole, 2,4-dimethylimidazole, 2-ethyl-4-methylimidazole, 2-phenylimidazole and 2-phenyl-4-methylimidazole, phosphine compounds such as triphenylphosphine, tributylphosphine, tri(p-methylphenyl)phosphine and tri(nonylphenyl)phosphine, phosphonium salts such as tetraphenylphosphonium tetraphenylborate and tetraphenylphosphonium tetranaphthoic acid borate, and betaine-like organic phosphorus compounds such as triphenyl phosphonio phenolate and a reaction product of benzoquinone and triphenylphosphine.

The use amount of the above hardening accelerator is not limited. It should be appropriately set in accordance with the function of the hardening accelerator.

The thermoset resin composition according to one embodiment of the present invention may further include an inorganic filler. Examples of the inorganic filler include amorphous silica, crystalline silica, alumina, glass, calcium silicate, calcium sulfate, calcium carbonate, magnesite, clay, talc, mica, magnesia, and barium sulfate. Among them, amorphous silica, crystalline silica and the like are preferred.

In order to increase the compounding amount of the filler while maintaining excellent formability, it is preferred to use a spherical filler that has a wide particle diameter distribution so as to enable dense filling. In this case, it is preferred to use a mixture of 5 to 40 wt % of a spherical inorganic filler having a small particle diameter of 0.1 to 3 µm and 60 to 95 wt % of a spherical inorganic filler having a large particle diameter of 5 to 30 µm.

When the thermoset resin composition according to one embodiment of the present invention contains an inorganic filler, the compounding amount of the inorganic filler is appropriately set in accordance with the type and intended use of the inorganic filler. The compounding amount of the inorganic filler may be, for example, but is not limited to, 60 mass % to 93 mass % to the whole of the thermoset resin composition.

If necessary, additives such as a solvent, coupling agent, release agent, coloring agent, flame retardant, stress reducing agent and thickener may be added to or preliminarily reacted with the thermoset resin composition according to one embodiment of the present invention for use. Examples of the coupling agent include a silane-based coupling agent such as vinyl silane-based, amino silane-based and epoxy silane-based coupling agent and a titanium-based coupling agent. Examples of the release agent include carnauba wax, paraffin wax, stearic acid, montanic acid, and carboxyl group-containing polyolefin wax. Carbon black and the like may be mentioned as the coloring agent. Examples of the flame retardant include halogenated epoxy resin, halide, and phosphorous compound and examples of an auxiliary flame retardant include antimony trioxide. Examples of the stress reducing agent include silicon rubber, modified nitrile rubber, modified butadiene rubber, and modified silicon oil.

A hardened material can be obtained by heating the thermoset resin composition according to one embodiment of the present invention. The hardened material according to one embodiment of the present invention has structural portions originated from the active ester resin having vinyl groups and is therefore excellent in the dielectric characteristics such as low permittivity and low dielectric tangent.

Moreover, the active ester resin (A) has a structure in which the vinylbenzyl groups are directly bonded to the aromatic nuclei, and therefore the molecular motion of carbon chains formed when the vinyl groups react to be polymerized is less likely to occur compared with that of vinylbenzyl ether introduced using hydroxyl groups. Accordingly, even when the hardened material according to one embodiment of the present invention is heated, the rotational motion and the like of the structural portions originated from the active ester resin (A) in the hardened material are unlikely to occur. Therefore, the hardened material according to one embodiment of the present invention readily has a high glass-transition temperature and can be excellent in the heat resistance and stability.

The temperature at which the thermoset resin composition according to one embodiment of the present invention is hardened is appropriately set in accordance with the composition of the hardened material. The temperature for heating may be, for example, but is not limited to, within a temperature range of 100° C. to 250° C.

Specific work for the hardening is also not limited. For example, the thermoset resin composition according to one embodiment of the present invention is diluted with a solvent as necessary, a base material is coated with the diluted solution thus obtained, and the solution is dried and hardened by heating. The hardened material (hardened material film) according to one embodiment of the present invention can be obtained by releasing the obtained hardened coating from the base material. A molded material can also be obtained by hardening the thermoset resin composition according to one embodiment of the present invention in a mold. The hardened material of the thermoset resin composition according to one embodiment of the present invention may be used as a binder or may also be used as a coating material, and a member that includes the hardened material may be used as a laminating material.

The interlayer insulating material according to one embodiment of the present invention is composed of the thermoset resin composition according to one embodiment of the present invention. For example, the thermoset resin composition according to one embodiment of the present invention may be dissolved in a solvent thereby to be a varnish for interlayer insulation, which is applied to a circuit substrate to obtain an insulating layer.

The obtained varnish for interlayer insulation is spread on a support film and thereafter heat-treated to be a film-like form, which can be an adhesive sheet for use as the interlayer insulating material. This adhesive sheet can be an interlayer insulating material in a multilayer printed wiring board. When the interlayer insulating material according to one embodiment of the present invention is used for sealing semiconductors, it is preferred that the thermoset resin composition contains an inorganic filler as described above.

The prepreg according to one embodiment of the present invention comprises a semi-hardened body of the thermoset resin composition according to one embodiment of the present invention and a fibrous reinforcing member. This prepreg can be an interlayer insulating material in a multilayer printed wiring board. Method of manufacturing the prepreg according to one embodiment of the present invention is not limited. The prepreg according to one embodiment of the present invention can be manufactured by adding a solvent, as necessary, to the thermoset resin composition according to one embodiment of the present invention into a varnish-like form, impregnating a fibrous reinforcing material with the varnish-like thermoset resin composition, and heat-treating them.

It should be appreciated that the embodiments heretofore explained are described to facilitate understanding of the present invention and are not described to limit the present invention. Therefore, it is intended that the elements disclosed in the above embodiments include all design changes and equivalents to fall within the technical scope of the present invention.

EXAMPLES

Hereinafter, the present invention will be described further specifically with reference to examples and the like, but the scope of the present invention is not limited to these examples and the like.

<Hydroxyl Equivalent>

The sample was acetylated with pyridine and excessive acetic anhydride, and the acetic acid generated from the acetic anhydride consumed by the hydroxyl groups of the sample was titrated with alcohol solution of potassium hydroxide to obtain the hydroxyl equivalent.

<GPC Analysis Condition>
(1) Use apparatus: "HLC-8320 GPC" available from Tosoh Corporation
(2) Columns: all available from Tosoh Corporation, "TSK gel super HZ4000" (one column)+"TSK gel super HZ3000" (one column)+"TSK gel super HZ2000" (two columns)+"TSK gel super HZ1000" (one column) (columns of 6.0 mm×15 cm were connected)
(3) Solvent: tetrahydrofuran
(4) Flow rate: 0.6 ml/min
(5) Temperature: 40° C.
(6) Detector: differential refractive index (RI) meter (RI detector built in the measurement apparatus "HLC-8320 GPC")

<FD-MS Analysis Condition>
(1) Apparatus: "JMS-T100GCV" available from JEOL Ltd.
(2) Cathode voltage: −10 kV
(3) Emitter current: 0 mA→35 mA (51.2 mA/min)
(4) Range of measured mass: m/z=10 to 2000 (Example 1) m/z=10 to 3000 (Example 5)

Example 1

Figure 1:
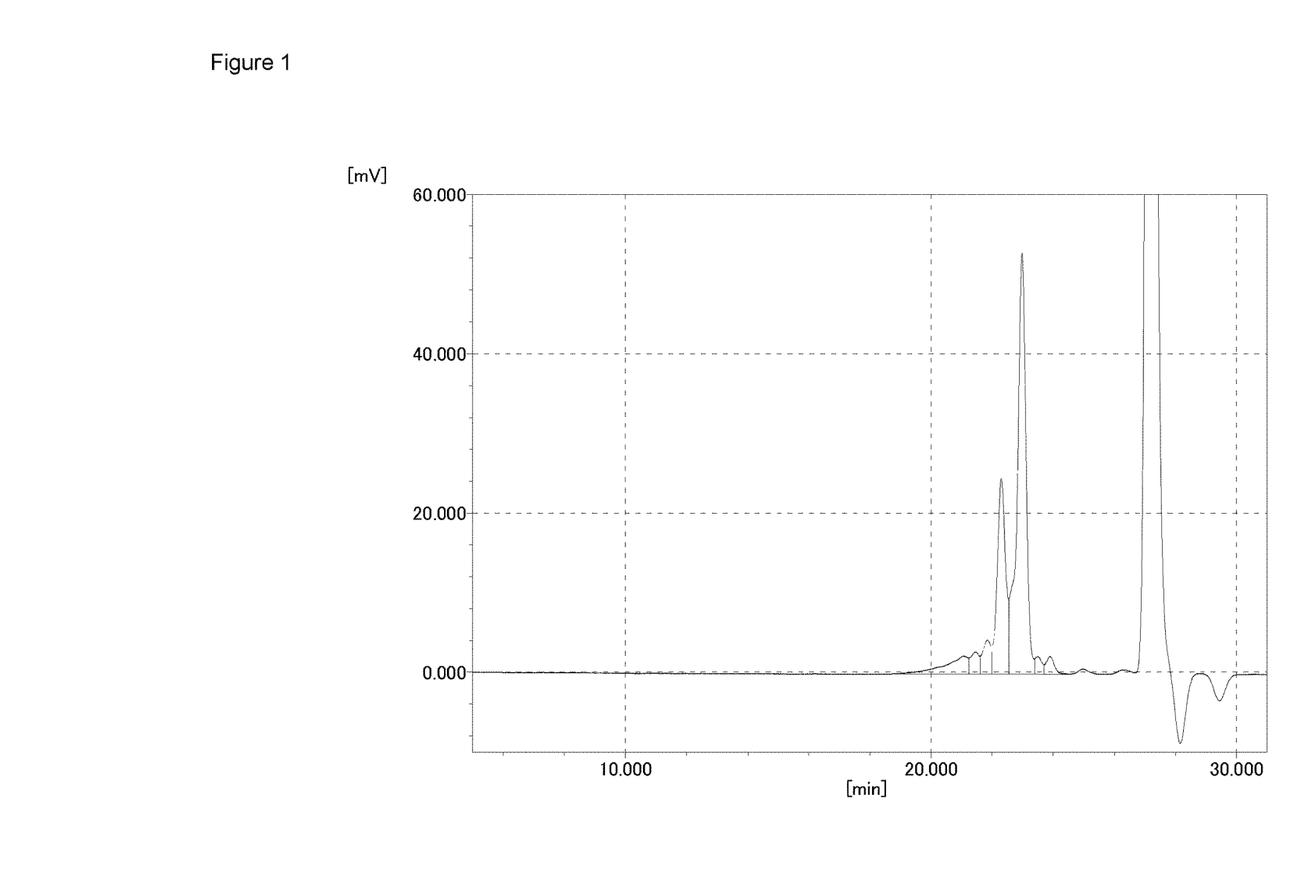
FIG. 1 is a GPC chart of a vinylbenzylated compound solution (A-1) obtained in Example 1.

Four-neck 2 L flask provided with a nitrogen gas introducing tube, thermometer and stirrer was charged with 160.2 g of 2,7-dihydroxynaphthalene, 311.0 g of the hydrotalcite ("KW-500SH" available from Kyowa Chemical Industry Co., Ltd.) and 1251.3 g of toluene, and they were heated to 60° C. to 70° C. Then, 152.6 g of chloromethylstyrene ("CMS-P" available from AGC SEIMI CHEMICAL CO., LTD.) were added by dropping while paying attention to rapid bubbling due to carbon dioxide gas. The temperature was further raised to 100° C. to 110° C. and the reaction was continued for 5 hours while discharging carbon dioxide gas and water to external of the system. The obtained reaction solution was filtrated to remove the hydrotalcite and the hydrotalcite was then washed with toluene thereby to obtain 1606.6 g of a vinylbenzylated compound solution (A-1) of 2,7-dihydroxynaphthalene. Solid content yield was 78.5%, solid content was 13.5%, and the hydroxyl equivalent was 144.5 g/eq. FIG. 1 illustrates a GPC chart of the obtained vinylbenzylated compound solution (A-1).

Figure 2:
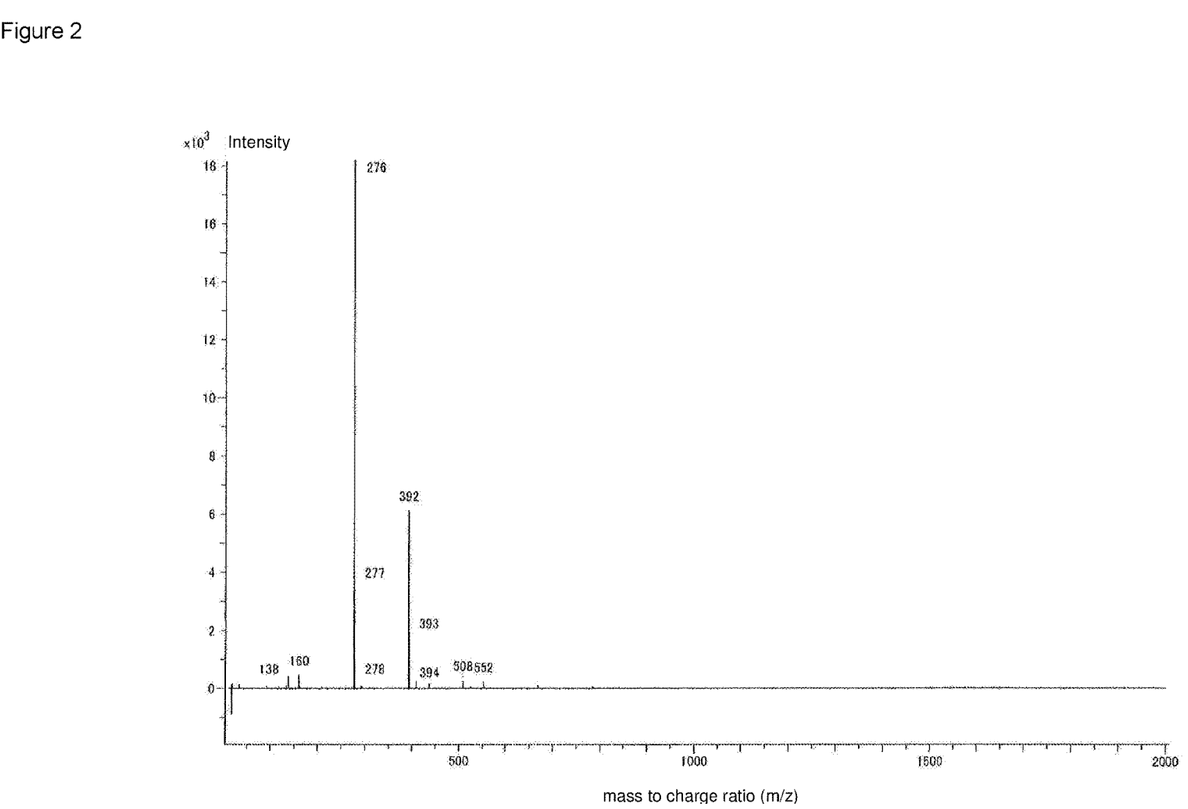
FIG. 2 is an FD-MS spectrum of the vinylbenzylated compound solution (A-1) obtained in Example 1.

FIG. 2 illustrates an FD-MS spectrum of the obtained vinylbenzylated compound solution (A-1). Peaks were detected, including a peak ($M^+$=276) representing one vinylbenzyl group (Mw: 116) being added to 2,7-dihydroxynaphthalene (Mw: 160), a peak ($M^+$=392) representing two vinylbenzyl groups (Mw: 116) being added, and a peak ($M^+$=508) representing three vinylbenzyl groups (Mw: 116) being added.

Therefore, it was confirmed to be a compound with one to three moles of vinylbenzyl groups being bonded to one mole of 2,7-dihydroxynaphthalene.

When the total amount of one mole of chloromethylstyrene is reacted with hydroxyl groups of one mole of 2,7-dihydroxynaphthalene, theoretical hydroxyl equivalent is 276 g/eq. On the other hand, when the total amount of one mole of chloromethylstyrene is reacted with aromatic nucleus side of one mole of 2,7-dihydroxynaphthalene, theoretical hydroxyl equivalent is 138 g/eq. It has thus been confirmed that a large part of the chloromethylstyrene is added to the aromatic nucleus side because the actually measured hydroxyl equivalent of the vinylbenzylated compound (A-1) is close to 138 g/eq.

Example 2

Four-neck 2 L flask provided with a nitrogen gas introducing tube, thermometer and stirrer was charged with 160.2 g of 1,6-dihydroxynaphthalene, 311.0 g of the hydrotalcite ("KW-500SH" available from Kyowa Chemical Industry Co., Ltd.) and 1251.3 g of toluene, and they were heated to 60° C. to 70° C. Then, 152.6 g of chloromethylstyrene ("CMS-P" available from AGC SEIMI CHEMICAL CO., LTD.) were added by dropping while paying attention to rapid bubbling due to carbon dioxide gas. The temperature was further raised to 100° C. to 110° C. and the reaction was continued for 5 hours while discharging carbon dioxide gas and water to external of the system. The obtained reaction solution was filtrated to remove the hydrotalcite and the hydrotalcite was then washed with toluene thereby to obtain 1646.1 g of a vinylbenzylated compound solution (A-2) of 1,6-dihydroxynaphthalene. Solid content yield was 79.0%, solid content was 13.3%, and the hydroxyl equivalent was 150.1 g/eq.

Example 3

Four-neck 2 L flask provided with a nitrogen gas introducing tube, thermometer and stirrer was charged with 208.3 g of 1,6-dihydroxynaphthalene, 412.2 g of the hydrotalcite ("KW-500SH" available from Kyowa Chemical Industry Co., Ltd.) and 948.9 g of methyl isobutyl ketone, and they were heated to 60° C. to 70° C. Then, 198.4 g of chloromethylstyrene ("CMS-P" available from AGC SEIMI CHEMICAL CO., LTD.) were added by dropping while paying attention to rapid bubbling due to carbon dioxide gas. The temperature was further raised to 100° C. to 115° C. and the reaction was continued for 5 hours while discharging carbon dioxide gas and water to external of the system. The obtained reaction solution was filtrated to remove the hydrotalcite and the hydrotalcite was then washed with methyl isobutyl ketone thereby to obtain 1401.4 g of a vinylbenzylated compound solution (A-3) of 1,6-dihydroxynaphthalene. Solid content yield was 83.1%, solid content was 21.3%, and the hydroxyl equivalent was 153.7 g/eq.

Example 4

Four-neck 2 L flask provided with a nitrogen gas introducing tube, thermometer and stirrer was charged with 128.2 g of 1,6-dihydroxynaphthalene, 157.0 g of the hydrotalcite ("KW-500SH" available from Kyowa Chemical Industry Co., Ltd.) and 385.4 g of methyl isobutyl ketone, and they were heated to 60° C. to 70° C. Then, 79.4 g of chloromethylstyrene ("CMS-P" available from AGC SEIMI CHEMICAL CO., LTD.) were added by dropping while paying attention to rapid bubbling due to carbon dioxide gas. The temperature was further raised to 100° C. to 115° C. and the reaction was continued for 5 hours while discharging carbon dioxide gas and water to external of the system. The obtained reaction solution was filtrated to remove the hydrotalcite and the hydrotalcite was then washed with methyl isobutyl ketone thereby to obtain 665.5 g of a vinylbenzylated compound solution (A-4) of 1,6-dihydroxynaphthalene. Solid content yield was 92.8%, solid content was 26.3%, and the hydroxyl equivalent was 127.3 g/eq.

Example 5

Figure 3:
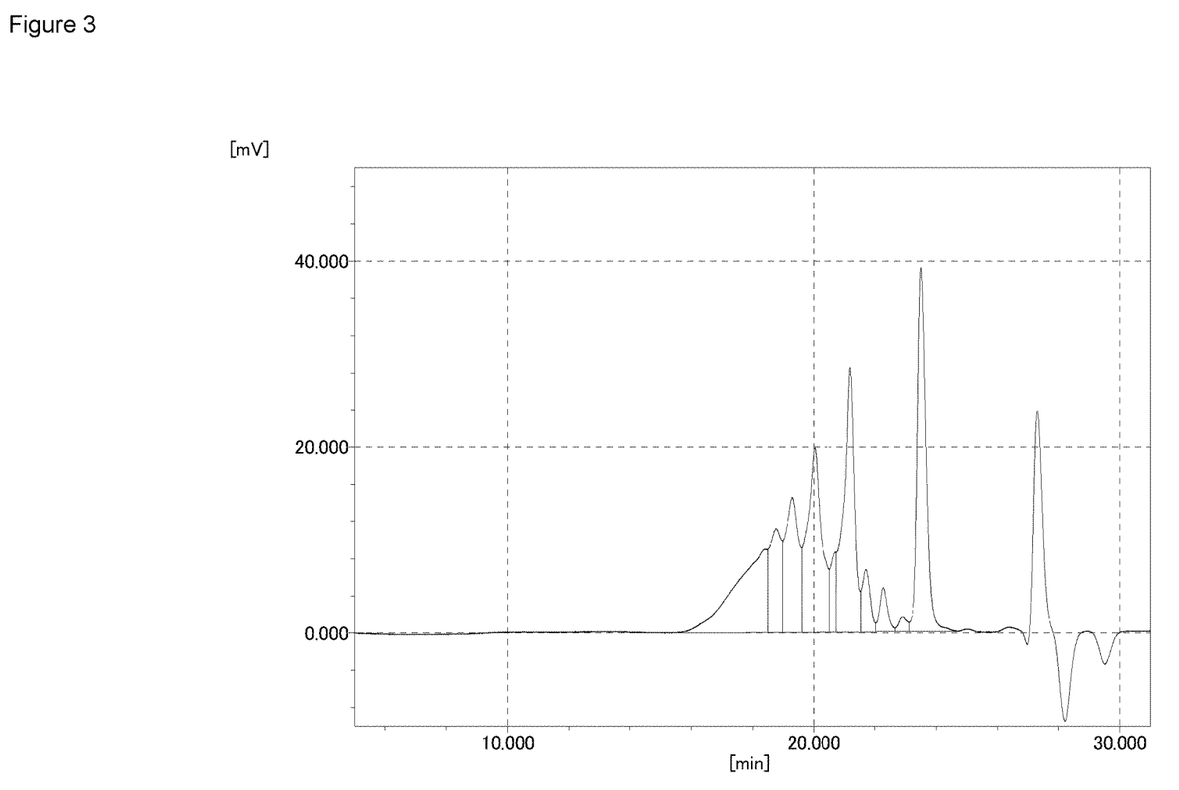
FIG. 3 is a GPC chart of a vinyl group-containing active ester resin solution (B-1) obtained in Example 5.

Four-neck 300 mL flask provided with a nitrogen gas introducing tube, thermometer and stirrer was charged with 190.0 g of the vinylbenzylated compound solution (A-1), 20.9 g of 1-naphthol and 0.6 g of tetra-n-butyl ammonium bromide, and they were dissolved at the room temperature. Then, after charging and dissolving 32.5 g of isophthalic chloride and dropping 64.1 g of 20% sodium hydroxide aqueous solution at a temperature within a range of 20° C. to 60° C., the reaction was performed for 6 hours at a temperature of 50° C. to 60° C. Further, after discharging a water layer separated by stationary placement, washing was performed with pure water until the pH became neutral. Thereafter, condensation was performed by distillation under reduced pressure, and a vinyl group-containing active ester resin solution (B-1) of a solid content of 67.7% and a theoretical functional group equivalent of 209 g/eq was obtained. FIG. 3 illustrates a GPC chart of the obtained vinyl group-containing active ester resin solution (B-1).

Figure 4:
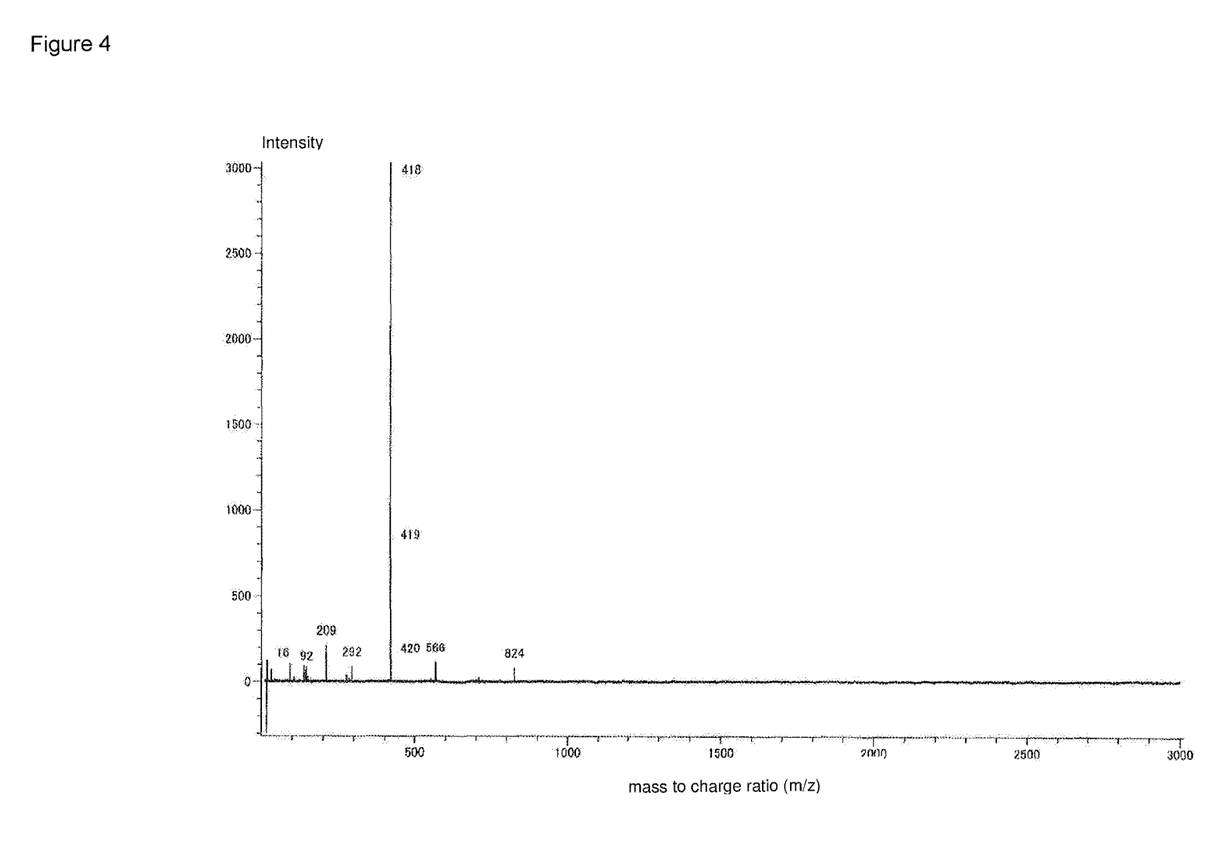
FIG. 4 is an FD-MS spectrum of the vinyl group-containing active ester resin solution (B-1) obtained in Example 5.

FIG. 4 illustrates an FD-MS spectrum of the obtained vinyl group-containing active ester resin solution (B-1). Peaks were detected, including a peak ($M^+$=418) corresponding to i=0 in General Formula (9) below and a peak ($M^+$=824) corresponding to i=1 and j=1.

Example 6

Four-neck 300 mL flask provided with a nitrogen gas introducing tube, thermometer and stirrer was charged with 190.0 g of the vinylbenzylated compound solution (A-2), 19.8 g of 1-naphthol and 0.6 g of tetra-n-butyl ammonium bromide, and they were dissolved at the room temperature. Then, after charging and dissolving 30.8 g of isophthalic chloride and dropping 60.7 g of 20% sodium hydroxide aqueous solution at a temperature within a range of 20° C. to 60° C., the reaction was performed for 6 hours at a temperature of 50° C. to 60° C. Further, after discharging a water layer separated by stationary placement, washing was performed with pure water until the pH became neutral. Thereafter, condensation was performed by distillation under reduced pressure, and a vinyl group-containing active ester resin solution (B-2) of a solid content of 65.2% and a theoretical functional group equivalent of 212 g/eq was obtained.

Example 7

Four-neck 2 L flask provided with a nitrogen gas introducing tube, thermometer and stirrer was charged with 400.0 g of the vinylbenzylated compound solution (A-3), 120.0 g of 1-naphthol and 233.4 g of methyl isobutyl ketone, and they were dissolved at the room temperature. Then, after charging and dissolving 140.2 g of isophthalic chloride and dropping 290.0 g of 20% sodium hydroxide aqueous solution at a temperature within a range of 20° C. to 40° C., the reaction was performed for 6 hours at a temperature of 30° C. to 40° C. Further, after discharging a water layer separated by stationary placement, washing was performed with pure water until the pH became neutral. Thereafter, methyl isobutyl ketone was distilled under reduced pressure while adding 158.9 g of cyclohexanone gradually, and a vinyl group-containing active ester resin solution (B-3) of a solid content of 61.3% and a theoretical functional group equivalent of 213 g/eq was obtained.

Example 8

Four-neck 300 mL flask provided with a nitrogen gas introducing tube, thermometer and stirrer was charged with 40.0 g of the vinylbenzylated compound solution (A-4), 22.1 g of 1-naphthol and 50.8 g of methyl isobutyl ketone, and they were diluted at the room temperature. Then, after charging and dissolving 23.7 g of isophthalic chloride and dropping 49.1 g of 20% sodium hydroxide aqueous solution at a temperature within a range of 20° C. to 40° C., the reaction was performed for 6 hours at a temperature of 30° C. to 40° C. Further, after discharging a water layer separated by stationary placement, washing was performed with pure water until the pH became neutral. Thereafter, methyl (9)

isobutyl ketone was distilled under reduced pressure while adding 25.8 g of cyclohexanone gradually, and a vinyl group-containing active ester resin solution (B-4) of a solid content of 79.1% and a theoretical functional group equivalent of 205 g/eq was obtained.

Example 9

Vinylbenzylation of 1,1'-methylenebis(2-naphthol)

Four-neck 500 mL flask provided with a nitrogen gas introducing tube, thermometer and stirrer was charged with 75.8 g of 1,1'-methylenebis(2-naphthol), 42.9 g of hydrotalcite ("KW-1000" available from Kyowa Chemical Industry Co., Ltd.) and 302.7 g of methyl-n-amyl ketone (hereinafter "MAK"), and they were heated to 60° C. to 70° C. Then, 25.0 g of chloromethylstyrene ("CMS-P" available from AGC SEIMI CHEMICAL CO., LTD.) were added by dropping while paying attention to rapid bubbling due to carbon dioxide gas. The temperature was further raised to 120° C. to 130° C. and the reaction was continued for 5 hours while discharging carbon dioxide gas and water to external of the system. The obtained reaction solution was filtrated to remove the hydrotalcite and the hydrotalcite was then washed with MAK thereby to obtain 431.8 g of a vinylbenzylated compound solution (A-5) of 1,1'-methylenebis(2-naphthol). Solid content yield was 94.6%, solid content was 20.8%, and the hydroxyl equivalent was 201.5 g/eq.

Example 10

Vinylbenzylation of naphthol zairock resin

Four-neck 2 L flask provided with a nitrogen gas introducing tube, thermometer and stirrer was charged with 172.0 g of naphthol zairock ("SN-485" available from NIPPON STEEL & SUMIKIN CHEMICAL CO., LTD.), 125.4 g of hydrotalcite ("KW-1000" available from Kyowa Chemical Industry Co., Ltd.) and 981.0 g of toluene, and they were heated to 60° C. to 70° C. Then, 73.3 g of chloromethylstyrene ("CMS-P" available from AGC SEIMI CHEMICAL CO., LTD.) were added by dropping while paying attention to rapid bubbling due to carbon dioxide gas. The temperature was further raised to 100° C. to 110° C. and the reaction was continued for 5 hours while discharging carbon dioxide gas and water to external of the system. The obtained reaction solution was filtrated to remove the hydrotalcite and the hydrotalcite was then washed with toluene thereby to obtain 1223.9 g of a vinylbenzylated compound solution (A-6) of naphthol zairock resin. Solid content yield was 92.7%, solid content was 17.3%, and the hydroxyl equivalent was 289.2 g/eq.

Example 11

Esterification product of vinylbenzylated 1,1'-methylenebis(2-naphthol)

Four-neck 300 mL flask provided with a nitrogen gas introducing tube, thermometer and stirrer was charged with 200.0 g of the vinylbenzylated compound solution (A-5), 36.4 g of 1-naphthol and 0.6 g of tetra-n-butyl ammonium bromide, and they were dissolved at the room temperature. Then, after charging and dissolving 46.5 g of isophthalic chloride and dropping 91.7 g of 20% sodium hydroxide aqueous solution at a temperature within a range of 20° C. to 40° C., the reaction was performed for 6 hours at a temperature of 50° C. to 60° C. Further, after discharging a water layer separated by stationary placement, washing was performed with pure water until the pH became neutral. Thereafter, condensation was performed by distillation under reduced pressure, and a vinyl group-containing active ester resin solution (B-5) of a solid content of 72.0% and a theoretical functional group equivalent of 235 g/eq was obtained.

Example 12

Esterification Product of Vinylbenzylated Naphthol Zairock Resin

Four-neck 500 mL flask provided with a nitrogen gas introducing tube, thermometer and stirrer was charged with 250.0 g of the vinylbenzylated compound solution (A-6), 39.9 g of 1-naphthol and 0.7 g of tetra-n-butyl ammonium bromide, and they were dissolved at the room temperature. Then, after charging and dissolving 43.3 g of isophthalic chloride and dropping 83.5 g of 20% sodium hydroxide aqueous solution at a temperature within a range of 20° C. to 40° C., the reaction was performed for 6 hours at a temperature of 50° C. to 60° C. Further, after discharging a water layer separated by stationary placement, washing was performed with pure water until the pH became neutral. Thereafter, condensation was performed by distillation under reduced pressure, and a vinyl group-containing active ester resin solution (B-6) of a solid content of 69.5% and a theoretical functional group equivalent of 260 g/eq was obtained.

Comparative Example 1

Four-neck 300 mL flask provided with a nitrogen gas introducing tube, thermometer and stirrer was charged with 36.1 g of 1-naphthol, 25.3 g of isophthalic chloride and 183.5 g of toluene, and they were dissolved at the room temperature. Then, after dropping 52.0 g of 20% sodium hydroxide aqueous solution at a temperature within a range of 20° C. to 60° C., the reaction was performed for 6 hours at a temperature of 50° C. to 60° C. Thereafter, the reaction liquid was cooled to the room temperature and the precipitated crystal was recovered by filtration. Further, the obtained crystal was washed with pure water, then dried under reduced pressure at 80° C. and dissolved in dimethyl acetamide, and an active ester compound solution (B-7) of a solid content of 30% was obtained. The theoretical functional group equivalent was 209 g/eq.

Comparative Example 2

Biphenyl aralkyl phenol resin ("HE200C-17" available from AIR WATER INC., ICI viscosity at 150° C.: 150 mPa·s, hydroxyl equivalent: 210 g/eq) was dissolved in methyl ethyl ketone (MEK) and a resin solution (B-8) of a solid content of 60% was obtained.

Examples 13 to 18 and Comparative Examples 3 and 4

Methyl ethyl ketone (MEK) solution of a solid content 75% of biphenyl aralkyl-type epoxy resin ("NC-3000H" available from Nippon Kayaku Co., Ltd., epoxy equivalent: 290 g/eq) and dimethyl aminopyridine (DMAP) were mixed with each of the resin solutions (B-1 to B-8) manufactured in Examples 5 to 8, 11 and 12 and Comparative Examples 1 and 2, and a resin composition varnish was produced. The compounding amount for manufacturing each resin composition varnish is listed in Table 1. The unit of the numeric value of the compounding amount shown in Table 1 is weight portion. Each resin composition varnish was applied to a copper foil gloss surface, dried at 100° C. for 8 minutes, and hardened at 200° C. for 6 hours. The hardened varnish was peeled off from the copper foil and a hardened material film (hardened material) having a film thickness of about 80 μm was obtained.

(Measurement of Glass-Transition Temperature Tg)

The hardened material film obtained in each of Examples 13 to 18 and Comparative Examples 3 and 4 was cut (cut out) into a predetermined size and used as a sample for measurement of the glass-transition temperature. The glass-transition temperature Tg of each sample was measured under the condition below:

measurement apparatus: thermal mechanical analyzer "TAM8310evo" available from Rigaku Corporation;
sample size: 5 mm width×15 mm length×0.080 mm (80 μm) thickness;
atmosphere: under nitrogen;
measurement temperature: 25° C. to 300° C.;
rate of temperature rise: 10° C./min, and
measurement mode: stretching.

(Evaluation of Dielectric Characteristics)

The hardened material film obtained in each of Examples 13 to 18 and Comparative Examples 3 and 4 was cut out into a predetermined size and used as a sample for measurement. The measurement apparatus below was used to measure the dielectric characteristics of each sample under the condition below:

measurement apparatus: "Network Analyzer E5071C" available from Keysight Technologies and a permittivity measuring apparatus utilizing a cavity resonator perturbation method available from Kanto Electronic Application and Development Inc;
frequency: 1 GHz; and
sample size: 2 mm width×100 mm length×0.080 mm (80 μm) thickness.

Evaluation results are listed in Table 1.

The invention claimed is:

1. A vinylbenzylated phenol compound represented by Formula (1) below, (1)

wherein, in the Formula (1),
$R^1$ to $R^5$ are each independently hydrogen or a methyl group;
p is an integer from 1 to 4; and
$Ar^0$ is a structure represented by Formula (2), Formula (3), or Formula (11) below:

(2)

(3)

(11)

TABLE 1

|  | Example 13 | Example 14 | Example 14 | Example 15 | Example 17 | Example 18 | Comparative Example 3 | Comparative Example 4 |
|---|---|---|---|---|---|---|---|---|
| B - 1 | 10.45 | | | | | | | |
| B - 2 | | 10.60 | | | | | | |
| B - 3 | | | 10.65 | | | | | |
| B - 4 | | | | 10.25 | | | | |
| B - 5 | | | | | 11.75 | | | |
| B - 6 | | | | | | 13.00 | | |
| B - 7 | | | | | | | 10.45 | |
| B - 8 | | | | | | | | 10.50 |
| NC - 3000H | 17.40 | 17.40 | 17.40 | 17.40 | 17.40 | 17.40 | 17.40 | 17.40 |
| DMAP | 0.08 | 0.08 | 0.08 | 0.08 | 0.09 | 0.09 | 0.08 | 0.08 |
| Glass-transition temperature (° C.) | 176 | 178 | 162 | 154 | 151 | 159 | 107 | 143 |
| Permittivity (1 GHz) | 3.00 | 2.97 | 2.99 | 3.01 | 3.01 | 3.05 | 2.99 | 3.21 |
| Dielectric tangent (1 GHz) | 0.0098 | 0.0092 | 0.0079 | 0.0083 | 0.0066 | 0.0074 | 0.0136 | 0.0218 | where Y in the Formula (3) is a direct bond, —CH$_2$—, —C(CH$_3$)$_2$—, —CH(CH$_3$)—, an ether bond, a fluorenyl group, a sulfone group, a cyclohexylidene group, a 3,3,5-trimethylcyclohexylidene group, —C(CF$_3$)$_2$—, —C(CH$_3$)(Ph)-, a structure represented by Formula (21) below, a structure represented by Formula (22) below, or a structure represented by Formula (23) below:

where R$^{26}$ to R$^{33}$ are each independently hydrogen or a methyl group, and where Z in the Formula (11) is a direct bond, —CH$_2$—, —C(CH$_3$)$_2$—, —CH(CH$_3$)—, —CH(Ph)-, —C(CH$_3$)(Ph)-, a fluorenyl group, a cyclohexylidene group, a 3,3,5-trimethylcyclohexylidene group, a structure represented by the Formula (21) above, a structure represented by the Formula (22) above, or a structure represented by the Formula (23) above.

2. A method of manufacturing the vinylbenzylated phenol compound according to claim 1, the method comprising:
reacting a bifunctional phenol compound and a vinylbenzyl halide compound using any hydrotalcite as a dehydrohalogenation agent;
wherein the bifunctional phenol compound is represented by Formula (4), Formula (5), or Formula (12) below:

where Y in the Formula (5) is a direct bond, —CH$_2$—, —C(CH$_3$)$_2$—, —CH(CH$_3$)—, an ether bond, a fluorenyl group, a sulfone group, a cyclohexylidene group, a 3,3,5-trimethylcyclohexylidene group, —C(CF$_3$)$_2$—, —C(CH$_3$)(Ph)-, a structure represented by Formula (21) below, a structure represented by Formula (22) below, or a structure represented by Formula (23) below:

where R$^{26}$ to R$^{33}$ are each independently hydrogen or a methyl group, and where Z in the Formula (12) is a direct bond, —CH$_2$—, —C(CH$_3$)$_2$—, —CH(CH$_3$)—, —CH(Ph)-, —C(CH$_3$)(Ph)-, a fluorenyl group, a cyclohexylidene group, a 3,3,5-trimethylcyclohexylidene group, a structure represented by the Formula (21) above, a structure represented by the Formula (22) above, or a structure represented by the Formula (23) above.

3. A method of manufacturing an active ester resin, comprising
reacting the vinylbenzylated phenol compound according to claim 1, a monofunctional phenol compound, and one or more compound selected from the group consisting of an aromatic nucleus-containing dicarboxylic acid and a halide compound thereof.

4. A composition comprising a plurality of compounds represented by Formula (1) below, wherein, in the Formula (1),
R$^1$ to R$^5$ are each independently hydrogen or a methyl group;
p represents an average number of vinylbenzene substituents per compound in the composition and ranges from 0.1 to 4; and
Ar$^0$ is a structure represented by Formula (2), Formula (3), or Formula (11) below:

(2)

(3)

(11)

where Y in the Formula (3) is a direct bond, —CH$_2$—, —C(CH$_3$)$_2$—, —CH(CH$_3$)—, an ether bond, a fluorenyl group, a sulfone group, a cyclohexylidene group, a 3,3,5-trimethylcyclohexylidene group, —C(CF$_3$)$_2$—, —C(CH$_3$)(Ph)-, a structure represented by Formula (21) below, a structure represented by Formula (22) below, or a structure represented by Formula (23) below:

(21)

(22)

(23)

where R$^{26}$ to R$^{33}$ are each independently hydrogen or a methyl group, and where Z in the Formula (11) is a direct bond, —CH$_2$—, —C(CH$_3$)$_2$—, —CH(CH$_3$)—, —CH(Ph)-, —C(CH$_3$)(Ph)-, a fluorenyl group, a cyclohexylidene group, a 3,3,5-trimethylcyclohexylidene group, a structure represented by the Formula (21) above, a structure represented by the Formula (22) above, or a structure represented by the Formula (23) above.

5. An active ester resin comprising a component represented by Formula (6) below, where, in the Formula (6), Ar$^1$ and Ar$^2$ are each independently a phenyl group, a phenyl group having from one to three alkyl groups each having from one to four carbon atoms on an aromatic nucleus, a naphthyl group, or a naphthyl group having from one to three alkyl groups each having from one to four carbon atoms on an aromatic nucleus;

n represents an average number of repeat units per molecule in the component and ranges from 0.5 to 30; and X is a structure represented by Formula (7), Formula (8), or Formula (13) below:

(7)

(8)

(13)

where, in the Formula (7), R$^1$ to R$^5$ are each independently hydrogen or a methyl group, and m represents an average number of vinylbenzene substituents per X structure in the component and ranges from 0.1 to 4, where, in the formula (8), R$^6$ to R$^{15}$ are each independently hydrogen or a methyl group, Y is a direct bond, —CH$_2$—, —C(CH$_3$)$_2$—, —CH(CH$_3$)—, an ether bond, a fluorenyl group, a sulfone group, a cyclohexylidene group, a 3,3,5-trimethylcyclohexylidene group, —C(CF$_3$)$_2$—, —C(CH$_3$)(Ph)-, a structure represented by Formula (21) below, a structure represented by Formula (22) below, or a structure represented by Formula (23) below, and l and k together represent an average number of vinylbenzene substituents per X structure in the component and each range from 0.1 to 2:

where $R^{26}$ to $R^{33}$ are each independently hydrogen or a methyl group, and where, in the Formula (13), $R^{16}$ to $R^{25}$ are each independently hydrogen or a methyl group, Z is a direct bond, —$CH_2$—, —$C(CH_3)_2$—, —$CH(CH_3)$—, —CH(Ph)-, —$C(CH_3)$(Ph)-, a fluorenyl group, a cyclohexylidene group, a 3,3,5-trimethylcyclohexylidene group, a structure represented by the Formula (21) above, a structure represented by the Formula (22) above, or the structure represented by Formula (23) above, and j and i together represent an average number of vinylbenzene substituents per X structure in the component and each range from 0.1 to 2.

6. The active ester resin as recited in claim 5, wherein X in the Formula (6) has a structure represented by the Formula (7).

7. A thermoset resin composition comprising:
the active ester resin according to claim 5; and
an epoxy resin.

8. The thermoset resin composition according to claim 7, further comprising
a hardening accelerator.

9. The thermoset resin composition according to claim 7, further comprising
an inorganic filler.

10. A hardened material of the thermoset resin composition according to claim 9.

11. An interlayer insulating material comprising the thermoset resin composition according to claim 9.

12. A prepreg comprising:
a semi-hardened body of the thermoset resin composition according to claim 9; and
a fibrous reinforcing member.

13. A method of manufacturing a prepreg, comprising impregnating a fibrous reinforcing material with the thermoset resin composition according to claim 9 and heating them so as to semi-harden the thermoset resin composition impregnated in the fibrous reinforcing material.

* * * * *